(12) United States Patent
Langhauser

(10) Patent No.: US 7,488,390 B2
(45) Date of Patent: Feb. 10, 2009

(54) CORN AND FIBER REFINING

(75) Inventor: Leon H. Langhauser, Decatur, IL (US)

(73) Assignee: Langhauser Associates, Inc., Decatur, IL (US)

( * ) Notice: Subject to any disclaimer, the term of this patent is extended or adjusted under 35 U.S.C. 154(b) by 0 days.

(21) Appl. No.: 12/229,784

(22) Filed: Aug. 27, 2008

(65) Prior Publication Data

US 2008/0318291 A1 Dec. 25, 2008

Related U.S. Application Data

(63) Continuation-in-part of application No. 11/336,324, filed on Jan. 20, 2006, now Pat. No. 7,452,425, which is a continuation-in-part of application No. 10/400,020, filed on Mar. 25, 2003, now abandoned.

(51) Int. Cl.
C12P 7/06 (2006.01)
(52) U.S. Cl. .............................. 127/40; 127/24; 127/27; 127/38; 127/43; 127/68; 426/482; 435/94; 435/96; 435/161
(58) Field of Classification Search ................... 127/24, 127/27, 38, 40, 43, 68; 426/482; 435/94, 435/96, 161
See application file for complete search history.

(56) References Cited

U.S. PATENT DOCUMENTS 4,361,651 A    11/1982  Keim .......................... 435/161
6,254,914 B1    7/2001  Singh et al. .................. 426/482
7,452,425 B1 *  11/2008  Langhauser ................... 127/40

OTHER PUBLICATIONS

"Fractionation of Lignocellulosic Biomass for Fuel-Grade Ethanol Production" by F.D. Guffey et al., Topical Report for Cooperative Agreement DE-FC26-98FT40323 Task 27 for the U.S. Department of Energy, Western Research Institute, Laramie, Wyoming, Oct. 2002.

* cited by examiner

Primary Examiner—David A Reifsnyder
(74) Attorney, Agent, or Firm—Philip L. Bateman

(57) ABSTRACT

Plant materials such as corn kernels which contain starch and fiber comprising cellulose, hemicellulose, lignin, and pectin are refined. The starch, cellulose, hemicellulose, and pectin are converted to sugars which are then fermented to ethanol. Additional sources of starch and fiber are optionally added to the refining process to further increase the yield of ethanol.

15 Claims, 9 Drawing Sheets

FIGURE ONE (PRIOR ART)
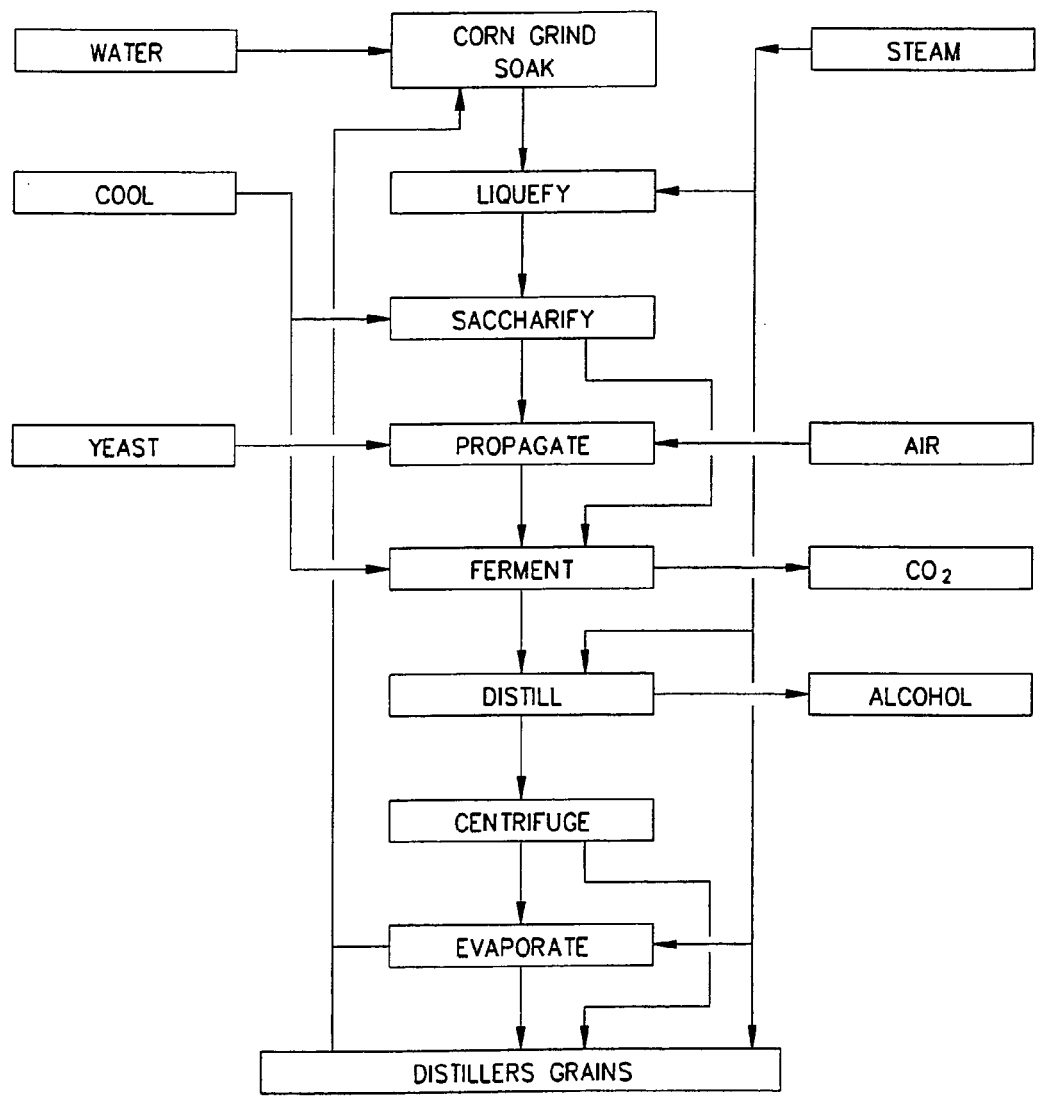

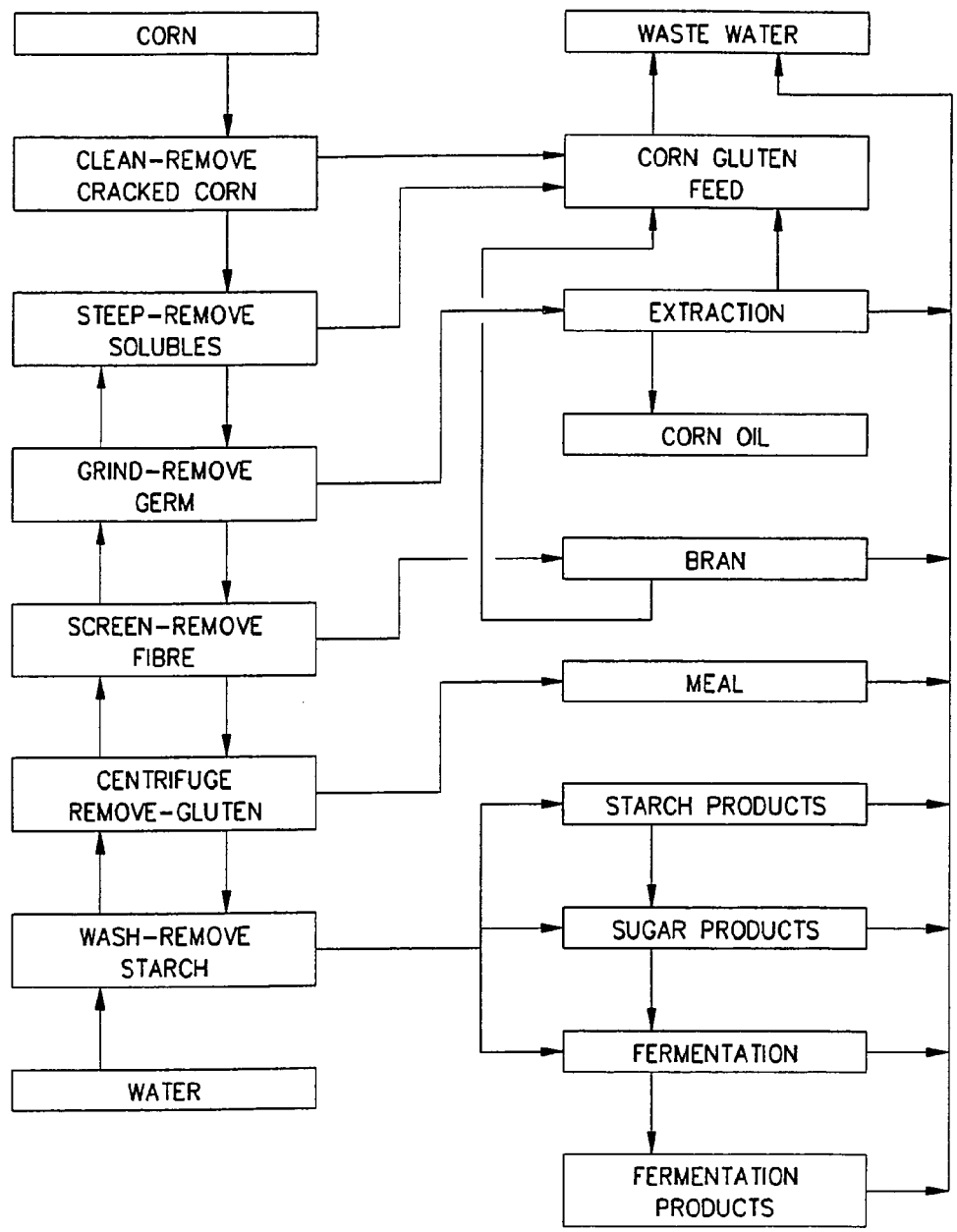
FIGURE TWO (PRIOR ART)

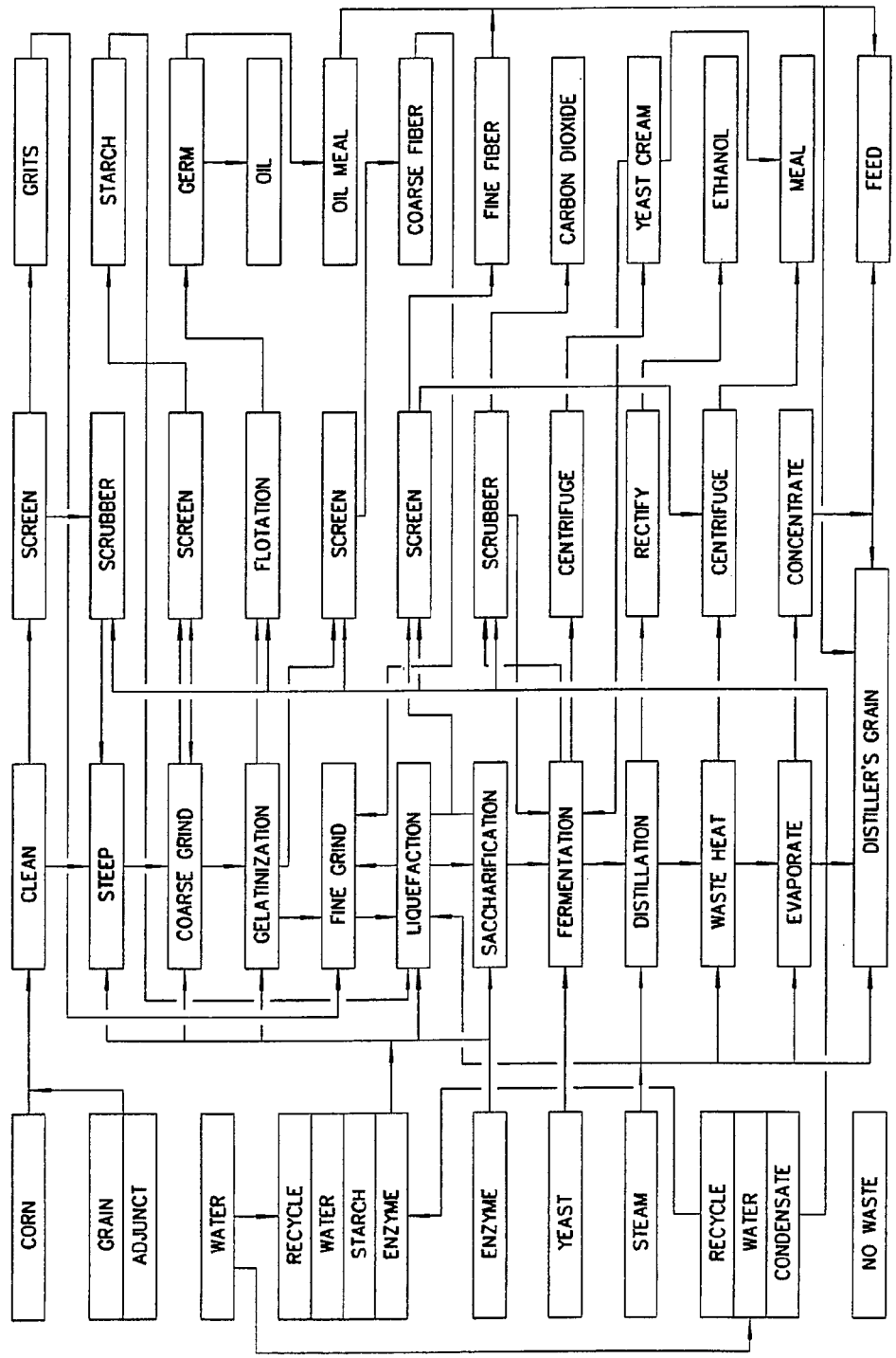
FIGURE THREE (PRIOR ART)

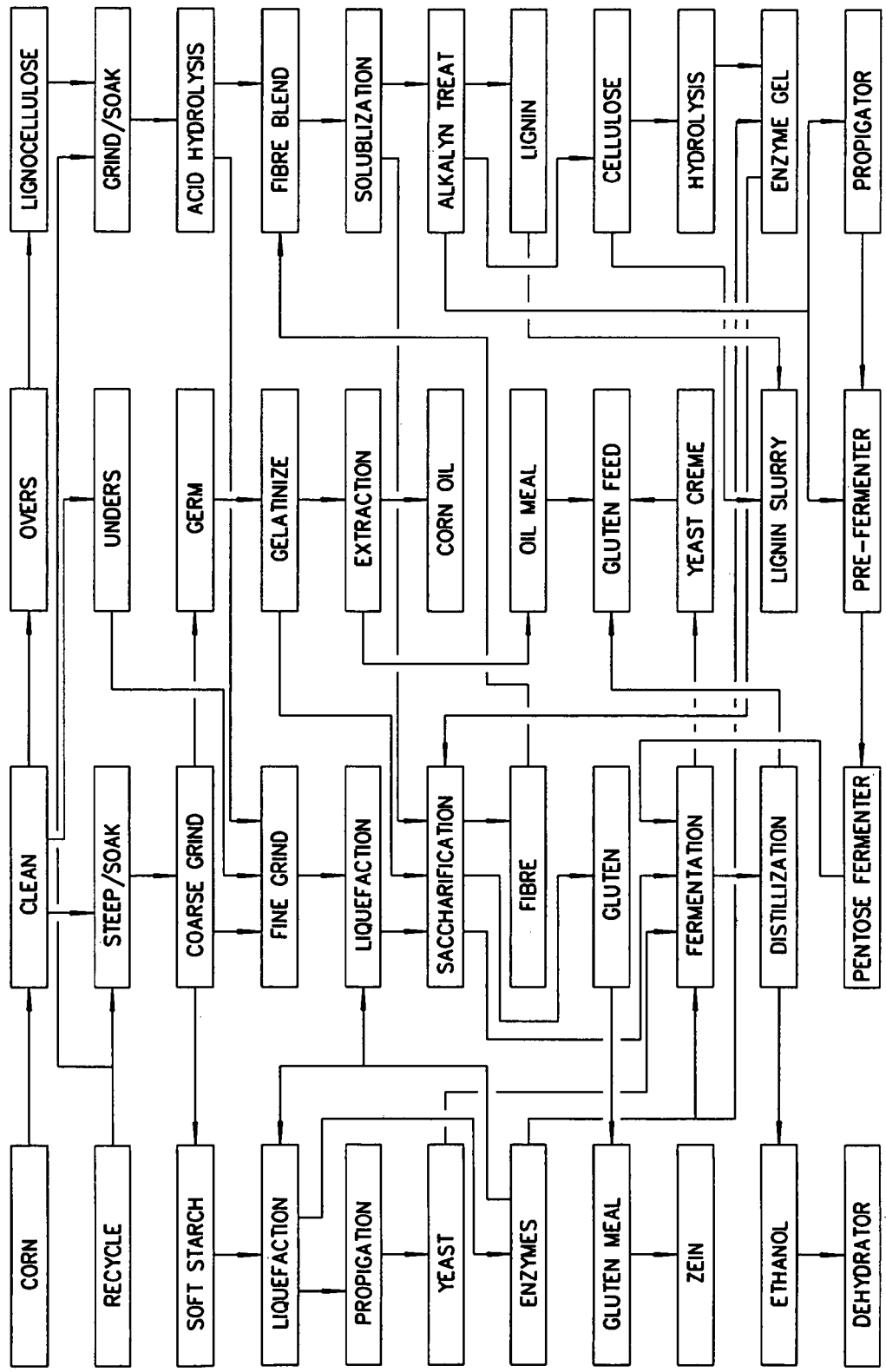
FIGURE FOUR

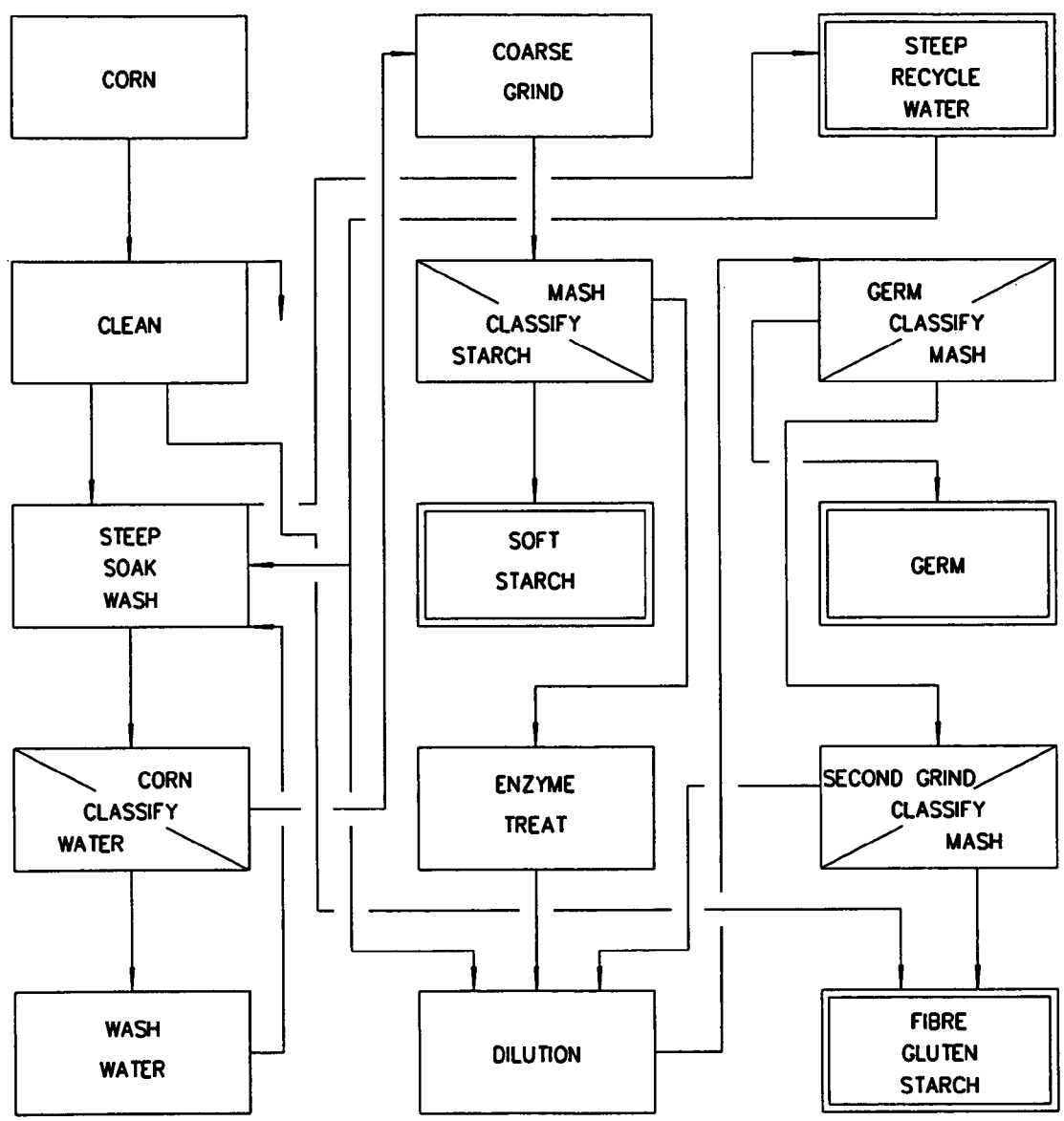
FIGURE FIVE

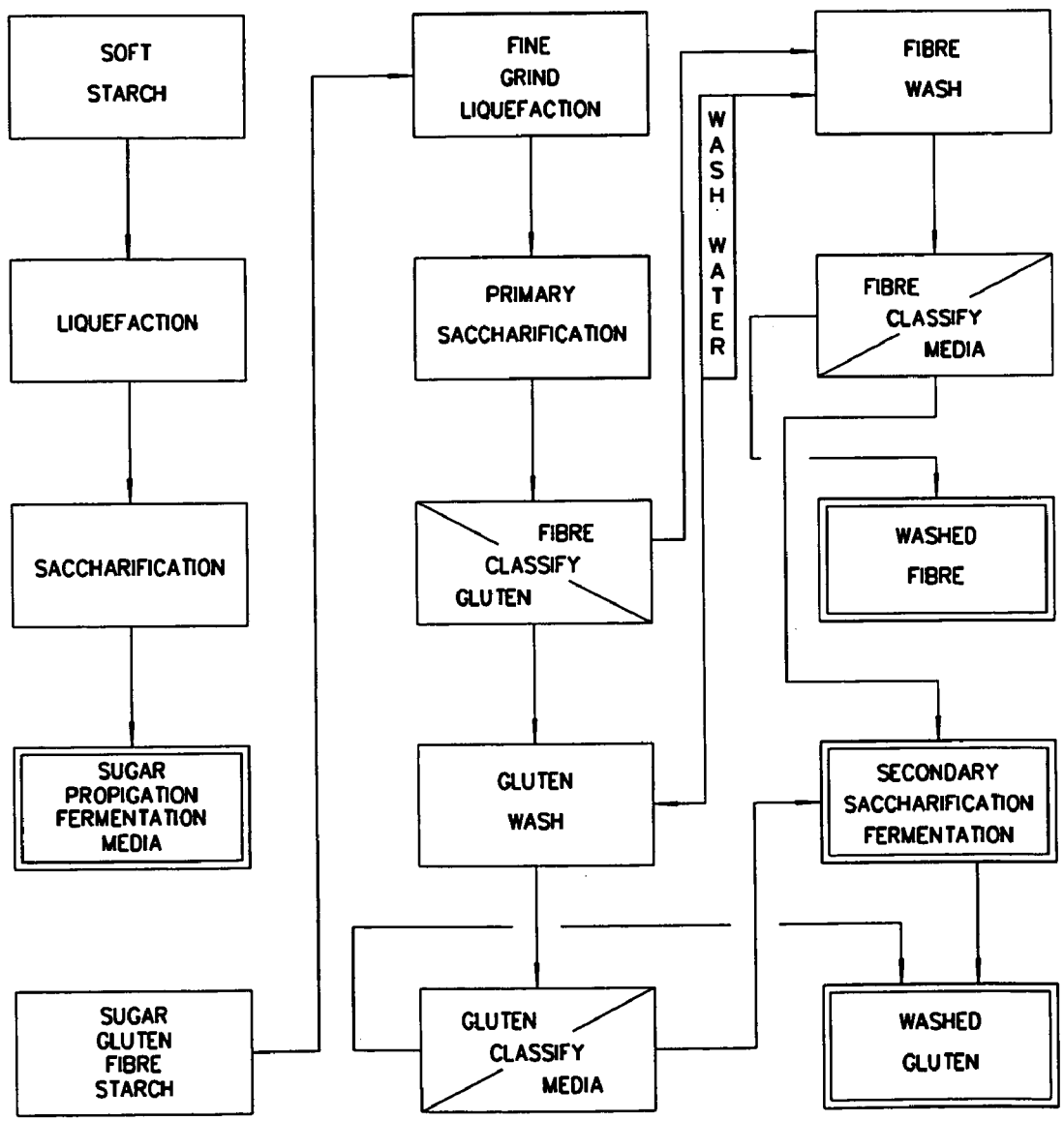
FIGURE SIX

FIGURE SEVEN
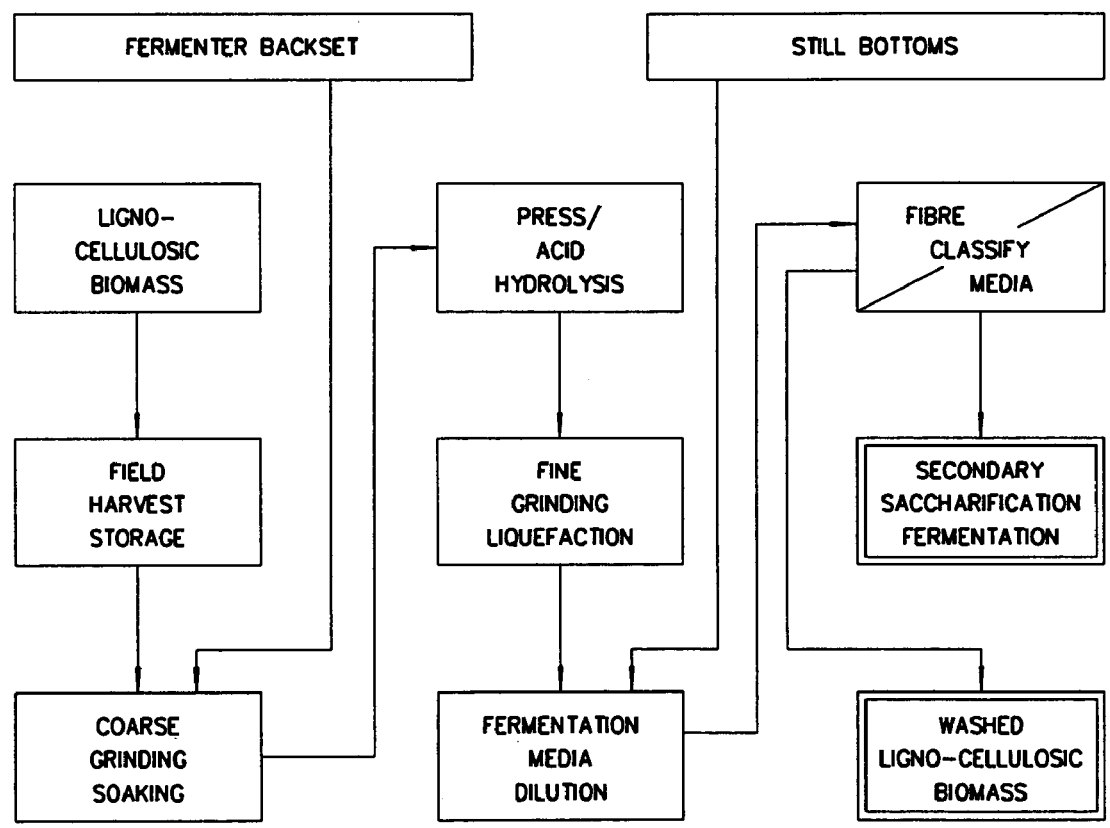

FIGURE EIGHT
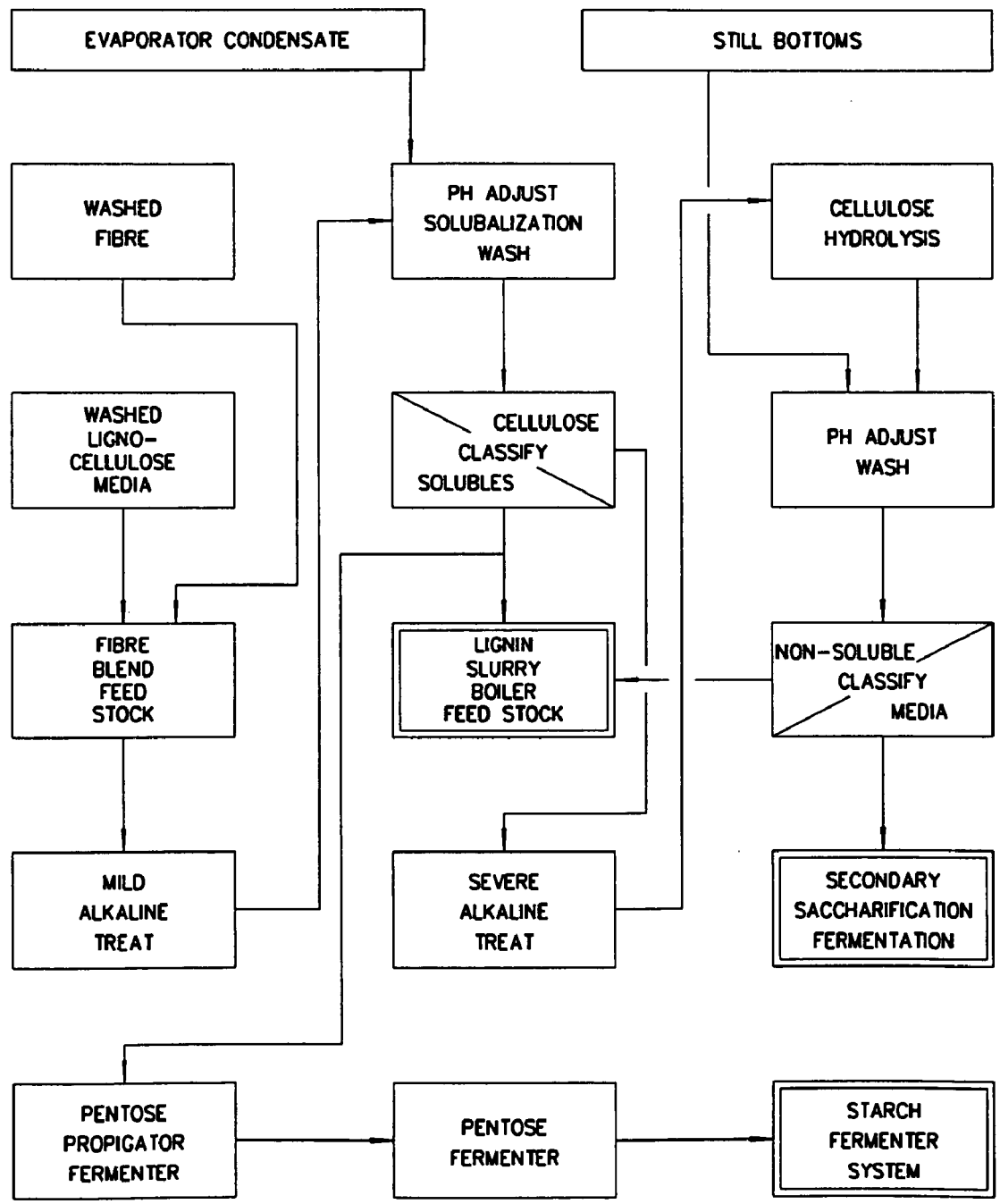

FIGURE NINE
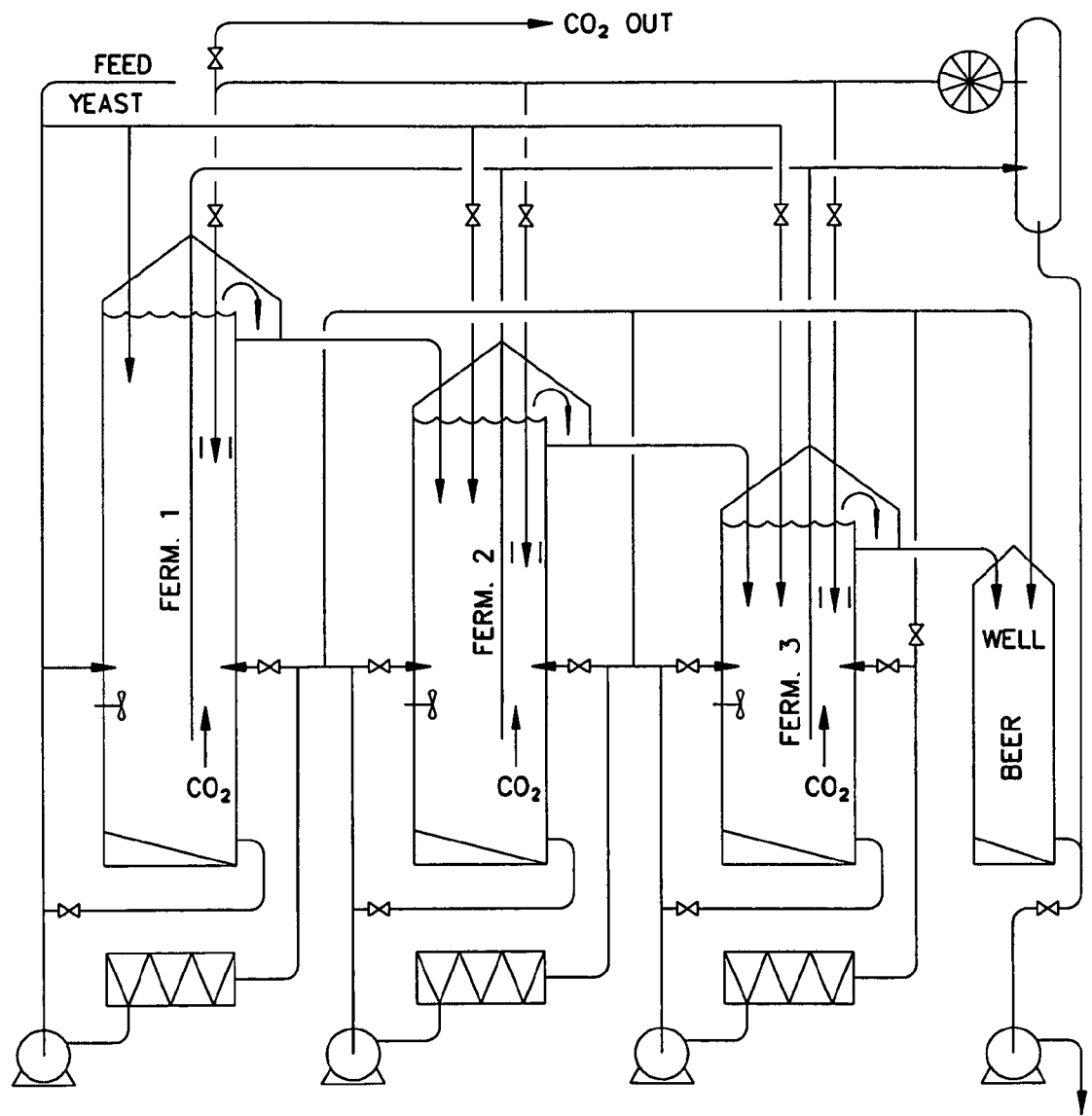

//<br>
CORN AND FIBER REFINING

CROSS-REFERENCE TO RELATED APPLICATIONS

This application is a continuation-in-part of U.S. patent application Ser. No. 11/336,324, Jan. 20, 2006, now U.S. Pat. No. 7,452,425 B1, which application was a continuation-in-part of U.S. patent application Ser. No. 10/400,020, filed Mar. 25, 2003, now abandoned.

FIELD OF THE INVENTION

This invention relates to chemistry. More particularly, this invention relates to the refining of corn and other plant materials.

BACKGROUND OF THE INVENTION

1. Corn

A variety of cereal grains and other plants are grown for use as food. Major cereal grains include corn, rice, wheat, barley, sorghum (milo), millets, oats, and rye. Other plants include potatoes, cassava, and artichokes. Corn is the most important cereal grain grown in the United States. Corn is sometimes called maize and has the scientific name *Zea mays*. A mature corn plant consists of a stalk with an ear of corn encased within a husk. The ear of corn consists of about 800 kernels on a cylindrical cob. The kernels are eaten whole and are also processed into a wide variety of food and industrial products. The other parts of the corn plant (i.e., the stalk, leaves, husk, and cob) are commonly used for animal feed, but are sometimes processed into a variety of food and industrial products.

In more detail, the corn kernel consist of three main parts: (1) the pericarp; (2) the endosperm; and (3) the germ. The pericarp (also known as the seed coat or bran) is the outer covering of the kernel. It consists primarily of relatively coarse fiber. The endosperm is the energy reserve for the plant. It consists primarily of starch, protein (also known as gluten), and small amounts of relatively fine fiber. The germ (also known as the embryo) consists primarily of oil and a miniature plant with a root-like portion and several embryonic leaves.

2. Starch

Starch is stored in a corn kernel in the form of discrete crystalline bodies known as granules. On a molecular level, starch is a polymer of anhydroglucose units ($C_6H_{10}O_5$). Anhydroglucose units combine with a water molecule ($H_2O$) to produce the common sugar glucose ($C_6H_{12}O_6$) so readily that starch is commonly referred to as a polymer of glucose. Starch is a member of the general class of carbohydrates known as polysaccharides. Polysaccharides contain multiple saccharide units (in contrast to disaccharides which contain two saccharide units and monosaccharides which contain a single saccharide unit). Polysaccharides made up of the same saccharide units (such as cellulose) are sometimes referred to as homopolysaccharides while polysaccharides made up of different saccharide units are sometimes referred to as heteropolysaccharides.

The length of a saccharide chain (the number of saccharide units in it) is sometimes described by stating its "degree of polymerization" (abbreviated to D.P.). Starch has a D.P. of 1000 or more. Maltose is a disaccharide (its D.P. is 2) that is composed of two glucose units. Glucose (also known as dextrose) is a monosaccharide (its D.P. is 1).

Saccharides having a D.P. of about 5 or less are sometimes referred to as sugars. Monosaccharide sugars containing six carbon atoms (e.g., glucose) are sometimes referred to as hexoses and sugars containing five carbon atoms are sometimes referred to as pentoses.

The anhydroglucose units in starch are connected to each other in one of two ways. When connected together in alpha-1,4-linkages, the starch molecule is linear. When connected together in alpha-1,6-linkages, a branch occurs. The relative number of the two linkages varies depending on the variety of corn. Both types of linkages are sometimes referred to as glucosidic linkages.

3. Fiber

As mentioned above, the pericarp and endosperm of the corn kernel contain fiber. The fiber comprises cellulose, hemicellulose, lignin, pectin, and relatively small amounts of other materials. Fiber is present in relatively small amounts in the corn kernel, but is present in much greater amounts in other corn components such as the cob, husk, leaves, and stalk. Fiber is also present in other plants. The combination of cellulose and lignin is sometimes known as lignocellulose and the combination of cellulose, lignin, and hemicellulose is sometimes known as lignocellulosic biomass. As used herein, the term "fiber" (and its alternative spelling "fibre") refers to cellulose, hemicellulose, lignin, and pectin. Each of the components of fiber is discussed in detail below.

Cellulose, like starch, is a polymer of anhydroglucose units ($C_6H_{10}O_5$). However, where the anhydroglucose units in starch are connected to each other in alpha-1,4 and alpha 1,6-linkages, the anhydroglucose units in cellulose are connected to each other in beta-1,4-linkages which give the cellulose molecule a linear, chain-like configuration. Cellulose is a rigid, crystalline structure because its molecules form attractions, known as hydrogen bonds, with adjoining molecules. Cellulose can be converted to glucose by breaking the beta-1,4-linkages by treatment with enzymes and/or by treatment at high temperatures and pressures in the presence of water.

The beta-1,4-linkages in cellulose are not broken down in the human digestive system. Accordingly, cellulose provides no nutritional benefit to humans and passes through the digestive system intact. Cellulose in the human diet is often referred to as fiber or roughage. In contrast to humans, some mammals are able to digest cellulose. Ruminant animals, such as cattle, sheep, goats, and deer, have certain types of bacteria in their digestive systems that produce enzymes that can break down the beta-1,4-linkages to free individual glucose molecules.

Hemicellulose is a heteropolysaccharide that, like cellulose, is present in the corn kernel and in the cell walls of other plants. On a molecular level, hemicellulose is a polymer of several pentose and hexose sugars, including xylose, mannose, galactose, arabinose, and glucose. Where cellulose molecules are linear and form a rigid crystalline structure, hemicellulose molecules are branched and form a much weaker structure.

Lignin is a complex compound composed of linked six-carbon phenolic rings that is present in the corn kernel and in the cell walls of other plants. After cellulose, lignin is the most abundant organic molecule on Earth. Lignin is a non-crystalline substance that acts as a binder of the cellulose in plants.

Pectin is heteropolysaccharide that is also present in cell walls. On a molecular level, pectin is a polymer of several compounds, including galacturonic acid, rhamnose, galactose, arabinose, and xylose.

4. Conventional Corn Refining Processes

A wide variety of processes have been used to separate the various components of corn. These separation processes are commonly known as corn refining. One of the processes is known as the dry milling process. In this process, the corn kernels are first cleaned and then soaked in water to increase their moisture content. The softened corn kernels are then ground in coarse mills to break the kernel into three basic types of pieces—pericarp, germ, and endosperm. The pieces are then screened to separate the relatively small pericarp and germ from the relatively large endosperm. The pericarp and the germ are then separated from each other. The germs are then dried and the oil is removed. The remaining germ is typically used for animal feed. The endosperm (containing most of the starch and protein from the kernel) is further processed in various ways. As described below, one of the ways is to convert the starch to glucose and then ferment the glucose to ethanol.

A second corn refining process is known as the wet milling process. In this process, the corn kernels are first cleaned and then steeped (soaked) in warm water containing sulfurous acid ($H_2SO_3$). During steeping, water soluble proteins and other substances dissolve into the steepwater. After steeping, the softened corn kernels are ground in coarse mills to break the kernel without damaging the germ. The kernels then flow to centrifugal separators which separate the less dense germs from the denser pericarp and endosperm. The germs are then dried and the oil is removed.

The pericarp and endosperm are then ground in fine mills. The finely ground stream flows to screens which separate the small particle size pericarp from the larger particle size endosperm. The endosperm stream then flows to centrifugal separators that separate the less dense protein from the denser starch. The finished starch is in granular form and is suitable for many different types of further processing.

For example, the starch can be dried and sold as unmodified starch. The starch can be modified and used for food or industrial purposes. The starch polymer can be partially hydrolyzed (i.e., shortened or reduced in D.P.) to produce corn syrup or hydrolyzed all the way to the individual glucose units. If completely hydrolyzed to glucose, the glucose molecules can be isomerized to fructose. Fructose is considerably sweeter than glucose and is widely used in the food industry. The starch can also be used for fermentation, as described in more detail below.

5. Fermentation

Fermentation is a process by which microorganisms such as yeast digest sugars to produce ethanol and carbon dioxide. The basic reaction is

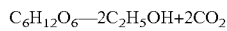

Yeast reproduce aerobically (oxygen is required) but can conduct fermentation anaerobically (without oxygen). The fermented mixture (commonly known as the beer mash) is then distilled to recover the ethanol. Distillation is a process in which a liquid mixture is heated to vaporize the components having the highest vapor pressures (lowest boiling points). The vapors are then condensed to produce a liquid that is enriched in the more volatile compounds.

Various processes have been disclosed for producing fuel ethanol from corn. The processes all convert the starch present in the corn kernel into glucose which is then fermented. For example, one process uses the endosperm isolated from a dry milling process as the feed material. This process is illustrated in FIG. 1. Another process uses the starch isolated from the wet milling process as its feed material. This process is illustrated in FIG. 2. Conventional processes for producing ethanol from corn produce a maximum of about 2.6 to 2.8 gallons of fuel ethanol per bushel of corn. Conventional processes do not convert any of the lignocellulose materials in corn to sugars and, therefore, the lignocellulose does not contribute to ethanol production.

6. The Langhauser Process

An efficient process for producing ethanol from corn is disclosed in Langhauser, U.S. Patent Application Publication No. 2004/0187863, Sep. 30, 2004, and Langhauser, U.S. patent application Ser. No. 11/336,324, Jan. 20, 2006, now U.S. Pat. No. 7,452,425 B1, both of which are hereby incorporated by reference in their entireties. The Langhauser process is illustrated in simplified form in FIG. 3. More detailed schematics of the Langhauser process are shown in FIGS. 5 and 6. By recovering increased amounts of starch, the Langhauser process produces about 2.85 gallons of fuel ethanol per bushel of corn.

The Langhauser process produces a coarse fiber stream (consisting of cellulose from the pericarp and various other pericarp components including hemicellulose, lignin, pectin, and sugars) as a co-product. Langhauser discloses that the coarse fiber stream can be treated in various ways. It can be steam exploded, expanded, chemically treated, treated with cellulase enzymes, or used for fermentation. The stream can also be further separated to produce cellulose, hemicellulose, lignin, and pectin.

The Langhauser process also produces a fine fiber stream (consisting primarily of cellulose from the endosperm). Langhauser discloses that the fine fiber stream can be used for human dietary fiber, oil and sugar extraction, alcohol fermentation, animal feed blends, or can be blended with other products.

7. The Guffey Process

A process for producing ethanol and specialty chemicals from lignocellulosic materials such as wood, agricultural residues, and paper wastes is disclosed in "Fractionation of Lignocellulosic Biomass for Fuel-Grade Ethanol Production" by F. D. Guffey et al., Topical Report for Cooperative Agreement DE-FC26-98FT40323 for the U.S. Department of Energy, Western Research Institute, Laramie, Wyo., October 2002.

In the Guffey process, a lignocellulosic feed stream consisting of water insoluble cellulose, hemicellulose, lignin, and pectin is first treated under mild alkaline conditions to solubilize the hemicellulose. The insolubles are then separated and treated under severe alkaline conditions to solubilize everything but the cellulose. The insoluble cellulose is then separated and treated with enzymes to produce glucose. The glucose is then fermented to ethanol.

8. Current Economic Conditions

As the world population and demand for fuels both increase, there is an increased demand for both food and ethanol from corn. It is estimated that approximately one-third of the corn grown in the United States in 2008 will be refined into ethanol. Some experts believe that the use of corn for ethanol is contributing to increased food prices. Accordingly, there is a demand for a process that greatly increases the yield of ethanol from a bushel of corn.

SUMMARY OF THE INVENTION

The general object of this invention is to provide an improved process for refining a plant material such as corn. A more particular object is to provide an improved process for refining corn into ethanol. Another more particular object is to provide an improved process for refining corn and other fiber-containing materials into ethanol.

I have invented a process for refining a plant material, the process comprising: (a) providing a plant material comprising: (i) starch; and (ii) fiber comprising cellulose, hemicellulose, lignin, and pectin; (b) isolating a starch slurry and a fiber slurry from the cereal grain; (c) converting the starch slurry to a primary glucose solution; (d) adding an effective amount of yeast to the primary glucose solution and fermenting it in a fermenter to produce carbon dioxide and a primary fermented stream containing ethanol; (e) heating the fiber slurry in a first reactor to a temperature of about 75 to 125° C. under mild alkaline conditions for a sufficient time to hydrolyze substantially all the hemicellulose and pectin into soluble pentose and hexose sugars; (f) separating the insoluble cellulose and lignin from the pentose and hexose sugar solution and forming a slurry of the cellulose and lignin; (g) adding the pentose and hexose sugar solution to the primary fermenter; (h) heating the slurry of cellulose and lignin in a second reactor to a temperature of about 125 to 160° C. under severe alkaline conditions for a sufficient time to hydrolyze substantially all the lignin into soluble lignin hydrolysates; (i) separating the insoluble cellulose, treating it with an effective amount of enzyme to convert it to a secondary glucose solution; and (j) adding the secondary glucose solution to the primary fermenter.

The process of this invention increases the yield of ethanol from a plant material such as corn by increasing the quantity of sugars that are fermented. The quantity of sugars is increased by converting the cellulose, hemicellulose, and pectin present in the plant material to pentose and hexose sugars.

BRIEF DESCRIPTION OF THE DRAWINGS

FIG. 1 is a schematic diagram of a prior art dry milling corn refining process.

FIG. 2 is a schematic diagram of a prior art wet milling corn refining process.

FIG. 3 is a schematic diagram of the Langhauser corn refining process.

FIG. 4 is a schematic diagram of the process of this invention.

FIG. 5 is a schematic diagram of the soaking, starch fractionation, and germ separation steps thereof.

FIG. 6 is a schematic diagram of the liquefaction, fiber separation, and gluten fractionation steps thereof.

FIG. 7 is a schematic diagram of the pretreatment step for additional fiber.

FIG. 8 is a schematic diagram of the fiber treatment steps.

FIG. 9 is a schematic diagram of the fermentation step.

DETAILED DESCRIPTION OF THE INVENTION

1. The Invention In General

The process of this invention refines corn, other cereal grains, and other plant materials into ethanol and other products. The process produces ethanol in yields significantly greater than those achieved in prior art processes. A preferred embodiment of the overall process is illustrated in simplified form in FIG. 4.

2. Raw Materials

The primary raw material for the process is a plant material containing starch and fiber. The preferred raw material is a fruit of a cereal grain. The most preferred raw material is corn kernels. The preferred corn kernels are United States grade number 2 yellow dent corn because of its large starch component and commercial availability. As discussed in detail above, corn kernels contain starch, protein, oil, and relatively small amounts of lignocellulose. If desired, the corn kernels are blended with the fruit of other cereal grains such as rice, wheat, barley, sorghum (milo), millets, oats, rye, and the like and/or with other plant materials such as potatoes, cassava, artichokes, and the like.

The process preferably includes a second source of starch and fiber (comprising cellulose, hemicellulose, lignin, and pectin) that is in addition to the fruit of a cereal grain. The second source preferably has a ratio of arabinoxylan to total non-starch polysaccharides (AX/NSP) of greater than 0.39. Suitable second sources include corn components other than the kernel, such as the cob, husk, leaves, and stalk. Other suitable second sources include plants such as miscanthus, switchgrass, and the like. Additional suitable second sources include co-products and by-products from the processing of cereal grains (e.g., wheat straw, barley straw, elevator dust from corn refining), wood (e.g., newsprint, cardboard, woodstock), nuts, cotton, sugar cane, sugar beets, and the like. In addition to starch and fiber, these second sources sometimes contain various other compounds, including free sugars, carboxymethyl cellulose, and mycotoxins (toxins produced by fungi).

The process optionally includes a third source of starch and fiber that is derived from the refining of the fruit of the cereal grain, but is typically not converted to ethanol. For example, the Langhauser process and other corn refining processes produce corn gluten feed and distiller's grain, both of which contain significant amounts of starch and fiber. Whether to sell these products or add them back for an increase in ethanol yield depends on economic factors.

3. Processing of the Corn Kernels

The plant materials are processed to convert starch to ethanol and to isolate and recover fiber. In the case of corn, the corn kernels are treated by a process that converts the starch into ethanol and that also isolates the coarse fiber from the pericarp and the fine fiber from the endosperm. The preferred corn process is the Langhauser process for many reasons, including its maximization of the amount of recovered fiber and minimization of the amount of starch associated with the recovered fiber. As previously mentioned, schematics of the Langhauser process are shown in FIGS. 3, 5, and 6.

The basic steps of the Langhauser corn refining process include the following: (1) providing corn kernels having a moisture content of about 10 to 30 percent and comprising: (i) a pericarp comprising coarse fiber; (ii) an endosperm comprising soft starch, hard starch, protein, and fine fiber; and (iii) a germ; (2) steeping the corn kernels in recycled water from downstream processes, which water has a temperature of about 50 to 70° C., is essentially free of sulfurous acid and contains effective amounts of amylase enzymes, in a counter-current steeping reactor for about 10 to 20 hours to produce an aqueous slurry of steeped corn kernels having a moisture content of about 40 to 50 percent; (3) coarsely grinding the steeped corn kernels to produce a coarsely ground stream comprising coarse fiber, soft starch, hard starch-protein-fine fiber fragments, and germs; (4) heating the coarsely ground stream in the presence of effective amounts of amylase enzymes to gelatinize starch clinging to the coarse fiber and germs and to produce a partially gelatinized stream; (5) removing the coarse fiber; (6) subjecting the partially gelatinized stream to sufficient shear and cavitation forces in the presence of effective amounts of amylase enzymes to gelatinize substantially all the starch and to produce a liquefied stream; (7) exposing the liquefied stream to effective amounts of amylase enzymes to produce a saccharified stream; (8) removing the fine fiber; (9) adding an effective amount of yeast to the saccharified stream and fermenting it to produce carbon dioxide and a fermented stream containing ethanol; (10) removing the carbon dioxide produced during fermentation and recycling some for gas lift agitation and blanketing; and (11) distilling the fermented stream to produce an ethanol stream and a bottoms stream.

4. Mild Alkaline Hydrolysis

The next step of the process of this invention is to combine the coarse fiber and the fine fiber into an aqueous fiber slurry. The fiber slurry is then subjected to a mild alkaline hydrolysis in a first reactor that converts the hemicellulose and pectin into soluble pentose and hexose sugars. A preferred embodiment of this step of the process is shown in FIG. 8. The hydrolysis is conducted until the hemicellulose and pectin are substantially dissolved. The term "substantially dissolved" means at least 90 percent of the hemicellulose and the pectin are soluble in 100° C. water.

The first hydrolysis is preferably performed by heating the fiber slurry to a temperature of about 75 to 125° C. (about 167 to 257° F.), preferably about 100° C. (about 212° F.), under mild alkaline conditions (a pH of about 8 to 10) at atmospheric pressure for a sufficient time, typically five or ten minutes, to hydrolyze substantially all the hemicellulose and pectin into soluble sugars. The first hydrolysis is performed in a suitable reaction vessel, such as a continuous plug flow reactor or a batch reactor.

5. First Separation of Solubles and Insolubles

After the first hydrolysis, a separation is made between the insoluble cellulose and lignin and the sugar solution containing both pentoses and hexoses. The separation is made using any suitable method of separating an insoluble component from a solution, including filtration, centrifugation, etc. The insolubles are preferentially washed with recycle blowdown from the starch fermentation system which also reduces the pH, but contains fine fiber and yeast which is preferentially separated with a standard decanter centrifuge. The centrate contains the pentose and hexose sugars with the soluble recycled solubles for addition to the fermenter system. If desired, the cellulose and lignin is partially recycled back to the front of the system which recycles alkaline base but more importantly greatly increases the fluidity of the fiber.

6. Prefermentation of Pentoses in Secondary Fermenter

The pentose and hexose sugar solution from the first separation can be added directly to the primary fermentation system. However, currently available strains of yeasts are not capable of high conversions of pentose to ethanol. Available strains can only produce low concentrations of ethanol. Accordingly, it is preferred to "preferment" the pentoses in a secondary fermenter and then add the partially fermented solution (containing pentoses, glucose, and hexoses) to the main fermenter system to take advantage of the operating cost savings. The term "secondary" refers to the fact that the secondary fermenter is smaller in capacity than the primary fermenter and not to its order in the process. The prefermentation system is a three stage continuous fermenter: (1) enzymes and aeration are added to the first stage to initiate saccharification and to propagate the yeast; (2) the second stage is the ethanol production log phase; and (3) the third stage is the decanting stage where the yeast is settled and returned to the first stage and the overflow ethanol is transferred to the main fermenter system. A simplified diagram of this step of the process is shown in FIG. 8.

7. Severe Alkaline Hydrolysis

The cellulose and lignin slurry from the first separation is subjected to a second hydrolysis in a second reactor to hydrolyze the lignin until it is substantially dissolved. The second hydrolysis is conducted under more severe conditions than the first hydrolysis. The temperature is generally about 125 to 160° C. (about 257 to 320° F.), preferably about 150° C. (about 302° F.). The second hydrolysis is performed in any suitable reaction vessel, including continuous plug flow reactors and batch reactors. It is preferably conducted in a co-rotating screw with steam injection with pressure of about 200 to 600 psi for about 3 to 20, preferably about 5 to 10, minutes. Holding times longer than about 20 minutes are generally undesirable because they decrease the glucose content. Calcium and sodium hydroxide are used to maintain the pH at least about 10. An oxidizing agent such as elemental oxygen can improve the breakdown of the lignin. This step of the process is illustrated in FIG. 8.

8. Second Separation of Solubles and Insolubles

After the second hydrolysis, a separation is made between the insoluble cellulose and the soluble lignin hydrolysates. This second separation is made using any suitable method of separating an insoluble component from a solution, including filtration, centrifugation, etc. The preferred method of separation is screening to salvage most of the alkaline slurry for recycle and washing of the smaller volume product and centrifugation with a standard decanter centrifuge.

9. Treatment of Cellulose

The insoluble material recovered from the second separation generally contains more than 99 percent cellulose. The cellulose is recovered or treated in any suitable manner. The cellulose is preferably converted to glucose at a temperature of about 160 to 175° C. (about 320 to 347° F.) at a pressure of 2 to 3 bars for about 20 minutes using conventional methods. The preferred conversion method is treatment with a cellulase and/or celluloase enzymes. After the cellulose is converted to glucose, it is added to the fermentation.

10. Treatment of Lignin Hydrolysates

The aqueous lignin hydrolysate solution is recovered from the second separation. If desired, certain components can be removed from the stream for separate treatment. The aqueous solution, whether or not certain components have been removed, is then heated to evaporate water. Water is removed until the solid material has a water content of less than about 50 to 60 weight percent. The solid material is then added to a liquid fuel, such as fuel oil, and burned. The heat produced by the burning is recovered and is used as desired.

11. Optional Addition of Second Source with Acid Hydrolysis

As previously mentioned, the process of this invention preferably includes one or more sources of starch and fiber in addition to the coarse fiber and fine fiber streams isolated from the refining of the corn kernels. These additional biomass sources are treated as follows.

The biomass is preferably slurried with still bottoms from distillation to reclaim the heat and contribute to the reduction of the pH requirements for acid hydrolysis and fine grinding. The total solids is reduced to about 15 weight percent, the conductivity controlled at 20-40,000 MLV (or approximately 1.8 to 2.0 pH) preferably with hydrochloric acid and hydrated at about 120 to 140° C. (about 248 to 284° F.) for 8 to 12 minutes holding time preferably using the Langhauser Supramyl process for acid liquefaction and fine grinding with a dextrose equivalent sugar conversion of about 18 to 24. The temperature is sufficient to kill or rupture objectionable microbes including without creating objectionable colors and protein products and fermentation inhibitors such as furfural or hydroxymethyl furfural on initiating the Mailard reaction and degradation of the sugars inhibiting enzyme conversion to dextrose.

The sugars and pectins are washed to the prefermentation process or the pre-saccharification step with more stillage bottoms and screened to reclaim cellulose, hemicellulose, lignin, and pectin. The liquefaction pH is reduced from about 5.5 to 6.0 to about 4.0 to 4.5 before cooling to control isomaltose, multulose, and pectin degrade floc formation etc. A preferred embodiment of this step of the process is illustrated in simplified form in FIG. 7.

12. Advantages

A major advantage of the process is that it increases the quantity of sugars that are fermented from a given bushel of corn and, thereby, increases the yield of ethanol. The quantity of sugars are increased in three ways. First the starch is liquefied and washed from the coproducts before fractionation. Second, sugars are hydrolyzed from cellulose, hemicellulose, and pectin and fermented with recycles for increased yields. And third, starches, cellulose, hemicellulose, and pectins from additional sources are processed to ethanol utilizing the same process system. The additional sources are processed with no additional water utilizing recycles, heat, chemicals and nutrients. A 30 percent increase in ethanol yield is easily attained.

Another major advantage is the utilization of the four major advantages of the Langhauser corn refining process. First, the process uses corn in the wide range of about 10 to 30 weight percent water for the process without the use of sulfurous acid. Accordingly, hazardous and/or malodorous sulfurs compounds are not released to the environment. Second, liquefaction with a rotary homogenizer provides simultaneous fine grinding. It also enables higher solids level (i.e., a reduced volume) and lower viscosity. Less steam, chemicals, enzymes, and process equipment are required because of the reduced volume. Higher sugar levels can be fed to the fermenter providing for higher ethanol concentrations and allows the blending of lower density pentose fermentations. Third, the process is generally conducted without the addition of ammonia or other nitrogen compounds for yeast propagation because sufficient nitrogen is made available by the action of protease enzymes on the protein in the corn. Accordingly, hazardous and/or malodorous nitrogen compounds are not released into the environment. And fourth, using recycled carbon dioxide for blanketing and gas lift agitation in the fermenter reactor reduces the fermentation losses caused by wild yeast and such bacteria as *Lactobacillus* and *Acetobacter*.

The process provides many additional advantages as well. For example, it produces greater amounts of ethanol per quantity of corn because the loss of starch in the products is reduced and recycles and nutrients can be utilized to process hemicellulose and cellulose. The process is carried out continuously rather than in a batch form Continuous processing is faster and more efficient and requires fewer additions of various chemicals during fermentation. It also produces products of greater quality and uniformity. The process is carried out at reduced maximum temperatures and holding times which not only improve costs but improves color and digestibilities of the products. The fractionated products are food grade products, the real answer to the Food VS Energy alternative choice.

I claim:

1. A process for refining a plant material, the process comprising:
    (a) providing a plant material comprising: (i) starch; and (ii) fiber comprising cellulose, hemicellulose, lignin, and pectin;
    (b) isolating a starch slurry and a fiber slurry from the plant material;
    (c) converting the starch slurry to a primary glucose solution;
    (d) adding an effective amount of yeast to the primary glucose solution and fermenting it in a primary fermenter to produce carbon dioxide and a primary fermented stream containing ethanol;
    (e) heating the fiber slurry in a first reactor to a temperature of about 75 to 125° C. under mild alkaline conditions for a sufficient time to hydrolyze substantially all the hemicellulose and pectin into soluble pentose and hexose sugars;
    (f) separating the insoluble cellulose and lignin from the pentose and hexose sugar solution and forming a slurry of the cellulose and lignin;
    (g) adding the pentose and hexose sugar solution to the primary fermenter;
    (h) heating the slurry of cellulose and lignin in a second reactor to a temperature of about 125 to 160° C. under severe alkaline conditions for a sufficient time to hydrolyze substantially all the lignin into soluble lignin hydrolysates;
    (i) separating the insoluble cellulose, treating it with an effective amount of enzyme to convert it to a secondary glucose solution; and
    (j) adding the secondary glucose solution to the primary fermenter.

2. The process of claim 1 wherein the plant material comprises corn.

3. The process of claim 2 additionally comprising the steps of: heating the lignin hydrolysate solution to evaporate water until a lignin hydrolysate concentrate having a moisture content of about 50 to 60 weight percent is produced; and burning the lignin hydrolysate concentrate to produce heat.

4. The process of claim 3 additionally comprising the steps of: adding an effective amount of yeast to the pentose and hexose sugar solution; fermenting the solution in a secondary fermented to produce carbon dioxide and a secondary fermented stream containing ethanol; and adding the secondary fermented stream to the primary fermenter.

5. The process of claim 4 additionally comprising the steps of: providing an additional source of starch and fiber comprising cellulose, hemicellulose, lignin, and pectin; forming an aqueous slurry; heating the slurry under mild acidic conditions for a sufficient time to hydrolyze substantially all the starch to glucose; separating the insoluble cellulose, hemicellulose, lignin, and pectin from the glucose solution; adding the glucose solution to the primary fermenter; and adding the cellulose, hemicellulose, lignin, and pectin to the first reactor.

6. The process of claim 5 wherein the additional source of starch and fiber is selected from the group consisting of corn cobs, corn husks, corn leaves, corn stalks, miscanthus, switchgrass, wheat straw, and barley straw.

7. A process for refining corn, the process comprising:
    (a) providing corn kernels comprising: (i) starch; and (ii) fiber comprising cellulose, hemicellulose, lignin, and pectin;
    (b) steeping the corn kernels in water that is essentially free of sulfurous acid at a temperature of about 50 to 75° C. for about 10 to 20 hours until the corn kernels have a moisture content of about 40 to 50 weight percent;
    (c) isolating a starch slurry and a fiber slurry from the steeped corn kernels;
    (d) converting the starch slurry to a primary glucose solution;
    (e) adding an effective amount of yeast to the primary glucose solution and fermenting it in a primary fermenter to produce carbon dioxide and a primary fermented stream containing ethanol;
    (f) heating the fiber slurry in a first reactor to a temperature of about 75 to 125° C. under mild alkaline conditions for a sufficient time to hydrolyze substantially all the hemicellulose and pectin into soluble pentose and hexose sugars;

(g) separating the insoluble cellulose and lignin from the pentose and hexose sugar solution and forming a slurry of the cellulose and lignin;

(h) adding an effective amount of yeast to the pentose and hexose sugar solution and fermenting it in a secondary fermenter to produce carbon dioxide and a secondary fermented stream containing ethanol;

(i) adding the secondary fermented stream to the primary fermenter;

(j) heating the slurry of cellulose and lignin in a second reactor to a temperature of about 125 to 160° C. under severe alkaline conditions for a sufficient time to hydrolyze substantially all the lignin into soluble lignin hydrolysates;

(k) separating the insoluble cellulose, treating it with an effective amount of enzyme to convert it to a secondary glucose solution;

(l) adding the secondary glucose solution to the primary fermenter;

(m) heating the lignin hydrolysate solution to evaporate water until a lignin hydrolysate concentrate having a moisture content of about 50 to 60 weight percent is produced; and (n) burning the lignin hydrolysate concentrate to produce heat.

8. The process of claim 7 additionally comprising the steps of: adding an effective amount of yeast to the pentose and hexose sugar solution; fermenting the solution in a secondary fermenter to produce carbon dioxide and a secondary fermented stream containing ethanol; and adding the secondary fermented stream to the primary fermenter.

9. The process of claim 8 additionally comprising the steps of: providing an additional source of starch and fiber comprising cellulose, hemicellulose, lignin, and pectin; forming an aqueous slurry; heating the slurry under mild acidic conditions for a sufficient time to hydrolyze substantially all the starch to glucose; separating the insoluble cellulose, hemicellulose, lignin, and pectin from the glucose solution; adding the glucose solution to the primary fermenter; and adding the cellulose, hemicellulose, lignin, and pectin to the first reactor.

10. The process of claim 9 wherein the additional source of starch and fiber is selected from the group consisting of corn cobs, corn husks, corn leaves, corn stalks, miscanthus, switchgrass, wheat straw, and barley straw.

11. A process for refining corn, the process comprising:

(a) providing corn kernels having a moisture content of about 10 to 30 percent and comprising: (i) a pericarp comprising coarse fiber; (ii) an endosperm comprising soft starch, hard starch, protein, and fine fiber; and (iii) a germ;

(b) steeping the corn kernels in recycled water from downstream processes, which water has a temperature of about 50 to 70° C., is essentially free of sulfurous acid and contains effective amounts of amylase enzymes, in a counter-current steeping reactor for about 10 to 20 hours to produce an aqueous slurry of steeped corn kernels having a moisture content of about 40 to 50 percent;

(c) coarsely grinding the steeped corn kernels to produce a coarsely ground stream comprising coarse fiber, soft starch, hard starch-protein-fine fiber fragments, and germs;

(d) heating the coarsely ground stream in the presence of effective amounts of amylase enzymes to gelatinize starch clinging to the coarse fiber and germs and to produce a partially gelatinized stream;

(e) recovering the coarse fiber from the partially gelatinized stream;

(f) subjecting the partially gelatinized stream to sufficient shear and cavitation forces in the presence of effective amounts of amylase enzymes to gelatinize substantially all the starch and to produce a liquefied stream;

(g) exposing the liquefied stream to effective amounts of amylase enzymes to produce a saccharified stream comprising glucose;

(h) recovering the fine fiber from the saccharified stream;

(i) adding an effective amount of yeast to the saccharified stream and fermenting it in a primary fermenter to produce carbon dioxide and a primary fermented stream containing ethanol;

(j) removing the carbon dioxide produced during fermentation and recycling some for gas lift agitation and blanketing;

(k) distilling primary the fermented stream to produce an ethanol stream and a bottoms stream;

(l) combining the removed coarse fiber and fine fiber to produce an aqueous fiber slurry comprising cellulose, hemicellulose, lignin, and pectin;

(m) heating the fiber slurry in a first reactor to a temperature of about 75 to 125° C. under mild alkaline conditions for a sufficient time to hydrolyze substantially all the hemicellulose and pectin into soluble pentose and hexose sugars;

(n) separating the insoluble cellulose and lignin from the pentose and hexose sugar solution and forming a slurry of the cellulose and lignin;

(o) adding an effective amount of yeast to the pentose and hexose sugar solution and fermenting it in a secondary fermenter to produce carbon dioxide and a secondary fermented stream containing ethanol;

(p) adding the secondary fermented stream to the primary fermenter;

(q) heating the slurry of cellulose and lignin in a second reactor to a temperature of about 125 to 160° C. under severe alkaline conditions for a sufficient time to hydrolyze substantially all the lignin into soluble lignin hydrolysates;

(r) separating the insoluble cellulose, treating it with an effective amount of enzyme to convert it to a secondary glucose solution;

(s) adding the secondary glucose solution to the primary fermenter;

(t) heating the lignin hydrolysate solution to evaporate water until a lignin hydrolysate concentrate having a moisture content of about 50 to 60 weight percent is produced; and (u) burning the lignin hydrolysate concentrate to produce heat.

12. The process of claim 11 additionally comprising the steps of: providing an additional source of starch and fiber comprising cellulose, hemicellulose, lignin, and pectin; forming an aqueous slurry; heating the slurry under acidic conditions for a sufficient time to hydrolyze substantially all the starch to glucose; separating the insoluble cellulose, hemicellulose, lignin, and pectin from the glucose solution; adding the glucose solution to the primary fermenter; and adding the cellulose, hemicellulose, lignin, and pectin to the first reactor.

13. The process of claim 12 wherein the additional source of starch and fiber is selected from the group consisting of corn cobs, corn husks, corn leaves, corn stalks, miscanthus, switchgrass, wheat straw, and barley straw.

14. The process of claim 13 wherein the cellulose is converted to a secondary glucose solution by treatment with enzyme at a temperature of about 160 to 175° C. at a pressure of 2 to 3 bars.

15. The process of claim 14 wherein the additional source of starch and fiber is hydrolyzed at a temperature of about 120 to 140° C. at a pH of about 1.8 to 2.0.

* * * * *